United States Patent
Henri et al.

(10) Patent No.: US 9,926,245 B2
(45) Date of Patent: Mar. 27, 2018

(54) FUELS AND CHEMICALS FROM LOWER ALKANES

(71) Applicant: Pioneer Energy Inc, Lakewood, CO (US)

(72) Inventors: John T Henri, Longmont, CO (US); Jan Zygmunt, Longmont, CO (US); Robert Zubrin, Golden, CO (US)

(73) Assignee: Pioneer Energy, Lakewood, CO (US)

( * ) Notice: Subject to any disclaimer, the term of this patent is extended or adjusted under 35 U.S.C. 154(b) by 0 days.

(21) Appl. No.: 14/500,712

(22) Filed: Sep. 29, 2014

(65) Prior Publication Data

US 2016/0200645 A1    Jul. 14, 2016

Related U.S. Application Data

(60) Provisional application No. 61/884,543, filed on Sep. 30, 2013.

(51) Int. Cl.

| | | |
|---|---|---|
| C07C 29/141 | (2006.01) |
| C07C 5/333 | (2006.01) |
| C07C 5/03 | (2006.01) |
| C07C 29/04 | (2006.01) |
| C07C 2/24 | (2006.01) |
| C10L 1/182 | (2006.01) |

(Continued)

(52) U.S. Cl.
CPC .............. *C07C 29/141* (2013.01); *C07C 2/32* (2013.01); *C07C 5/3335* (2013.01); *C07C 29/145* (2013.01); *C07C 45/34* (2013.01); *C10L 1/1824* (2013.01); *C07C 2523/85* (2013.01); *C07C 2531/16* (2013.01); *C10L 2200/0423* (2013.01); *C10L 2270/023* (2013.01); *Y02P 20/52* (2015.11)

(58) Field of Classification Search
CPC combination set(s) only.
See application file for complete search history.

(56) References Cited

U.S. PATENT DOCUMENTS

| | | | | |
|---|---|---|---|---|
| 5,446,213 A | * | 8/1995 | Sato .......................... | C07C 2/30 |
| | | | | 524/296 |
| 2008/0216391 A1 | * | 9/2008 | Cortright ................. | C10G 3/45 |
| | | | | 44/307 |

(Continued)

OTHER PUBLICATIONS

"Alcohol Synthesis by Carbonyl Compound Reduction", Sep. 28, 2006.*
"Ketone Synthesis by Oxidation of Alkenes", May 17, 2006.*

*Primary Examiner* — Ellen McAvoy
*Assistant Examiner* — Chantel Graham
(74) *Attorney, Agent, or Firm* — John T. Henri

(57) ABSTRACT

Methods to synthesize fuels and chemicals from natural gas liquids are described. Higher alcohols are synthesized starting from natural gas liquid compounds by converting an alkane from a NGL to an olefin, dimerizing said olefin, and, hydrating said olefin product to form a higher alcohol. Higher alcohols are synthesized starting from natural gas liquid compounds by converting an alkane from a NGL to an olefin, oxidizing the olefin to form a ketone or aldehyde and, hydrogenating the aldehyde or ketone product to form a higher alcohol. Thus, NGL component butane may be dehydrogenated to form butane, butylene is oxidized in the presence of a catalyst to form methylethyl ketone and methylethyl ketone hydrogenated to form butanol.

12 Claims, 4 Drawing Sheets

(51) Int. Cl.
*C07C 29/145* (2006.01)
*C07C 45/34* (2006.01)
*C07C 2/32* (2006.01)

(56) References Cited

U.S. PATENT DOCUMENTS

| | | | | |
|---|---|---|---|---|
| 2011/0046422 | A1* | 2/2011 | McAuliffe | C10L 1/04 585/16 |
| 2013/0139430 | A1* | 6/2013 | Fabre | C10L 1/14 44/322 |

\* cited by examiner

FUELS AND CHEMICALS FROM LOWER ALKANES

RELATED APPLICATIONS

This application claims the benefit of U.S. Provisional Application No. 61/884,543 filed 30 Sep. 2013 entitled "Fuels and Chemicals from Lower Alkanes" which is incorporated herein by reference.

BACKGROUND OF THE INVENTION

Petroleum is a vital source of fuels for transportation, industrial chemicals that produce polymers, plastics, pharmaceuticals, paints and other important chemicals. Recently, technologies have emerged that indicate vast new resources of hydrocarbons that are being recovered by hydraulic fracturing. Currently liquid-rich raw natural gas is being flared in large quantities at numerous locations by oil producers. This activity entails massive loss of income. Furthermore, the large-scale flaring of natural gas has raised environmental issues that could cause state and/or federal regulators to take action to close such operations down.

There is therefore an important need for a solution to address the problems mentioned above. The present invention addresses these issues and is a novel method to synthesize fuels and chemicals from lower hydrocarbons.

DETAILED DESCRIPTION OF THE INVENTION

An important aspect of the present invention is the synthesis of higher alcohols from natural gas liquids by dehydrogenation, oxidation and hydrogenation. Ethane, propane and butane obtained from natural gas liquids are dehydrogenated to form olefins which are oxidized to form olefins such as ethylene, propylene, 1-butylene and 2-butylene which are oxidized to form acetaldehyde, acetone and 2-butanone which are hydrogenated to form ethanol, isopropanol, and 2-butanol respectively. In one aspect the ethane, propane and butane are separated and subjected to the steps of dehydrogenation, oxidation and hydrogenation to form a single alcohol product. In one aspect the process comprises formation of ketones or aldehydes from ethane, propane or butane by the steps of dehydrogenation and oxidation. In one aspect the oxidation step is a Wacker oxidation which uses a palladium catalyst, copper salts such as copper chloride, oxygen and water as solvent. In one aspect the catalyst used for hydrogenation of the acetaldehyde and ketone products is a transition metal. In one embodiment the catalyst may be a ruthenium, platinum, palladium, copper, copper-zinc oxide, copper chromite, organometallic ruthenium and the like.

Another aspect of the present invention is a process to convert lower hydrocarbons such as ethane, propane, butane to higher molecular weight products such as butanol, hexanol, octanes and octanols. In one aspect of the invention, ethylene derived from dehydrogenation of ethane is dimerized to form butylenes which are subjected to hydration to form butanol. In one embodiment of the invention the invention a mixture of ethane, propane and butane are dehydrogenated to form ethylene, propylene and butene which are oxidized to form acetaldehyde, acetone or propanaldehyde and butanone or butyraldehyde respectively. The aforementioned mixture of carbonyl compounds maybe hydrogenated to form ethanol, propanol and butanol. In one aspect of the invention, ethylene derived from dehydrogenation of ethane is dimerized to form butylenes which are subjected to oxidation to form 2-butanone. In a variation of the embodiment the 2-butanone is hydrogenated of form butanol. In another aspect, a mixture of ethane, propane and butane are dehydrogenated to form ethylene, propylene and 1-butene and 2-butenes respectively, which are hydrated to form ethanol, propanol and butanols. In another aspect of the invention a lower alkane hydrocarbon such as ethane, propane or butane is dehydrogenated to form an unsaturated hydrocarbon which is subjected to successive dimerization reactions to form C-8, C12, C16 olefins which are used as fuels after hydrogenation.

DESCRIPTION OF DRAWINGS

Figure 1:
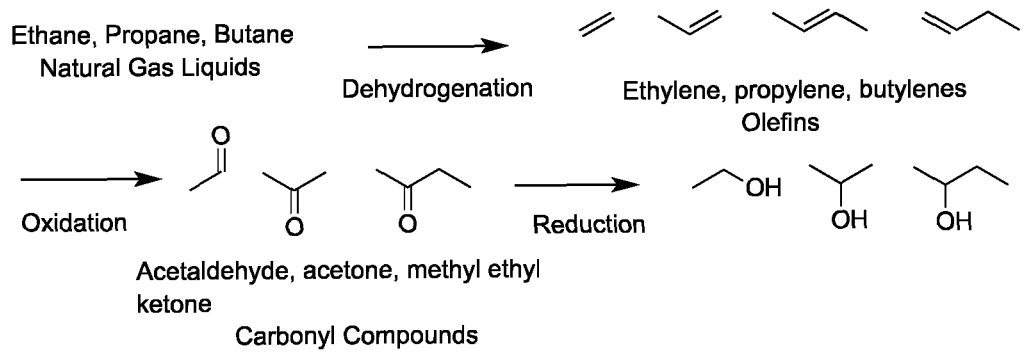
FIG. 1 Synthesis of higher alcohols from natural gas liquids by dehydrogenation, oxidation and hydrogenation.
Figure 2:
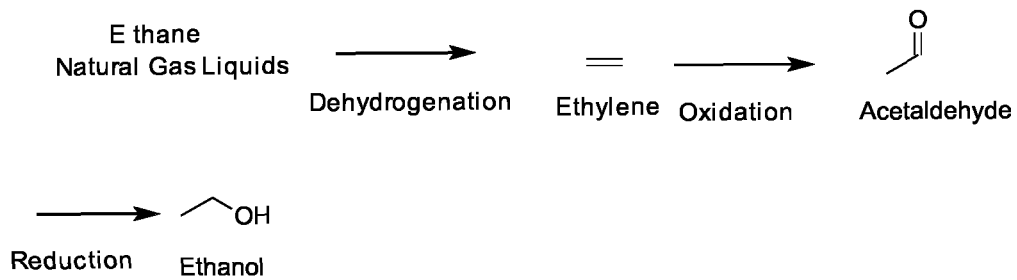
FIG. 2 Synthesis of alcohol from ethane by dehydrogenation, oxidation and hydrogenation.
Figure 3:
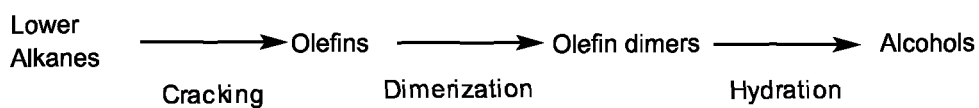
FIG. 3 Synthesis of Higher Alcohols from Natural Gas Liquids.
Figure 4:
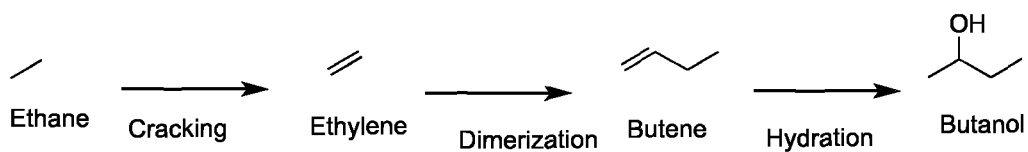
FIG. 4 Synthesis of butanol from ethane.
Figure 5:
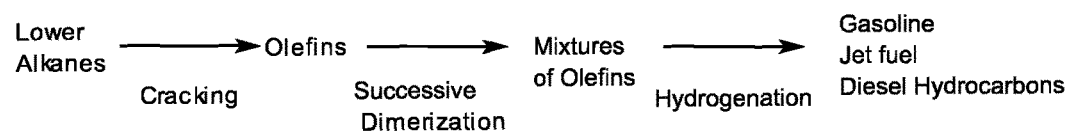
FIG. 5 Synthesis of fuels from natural gas liquids.
Figure 6:
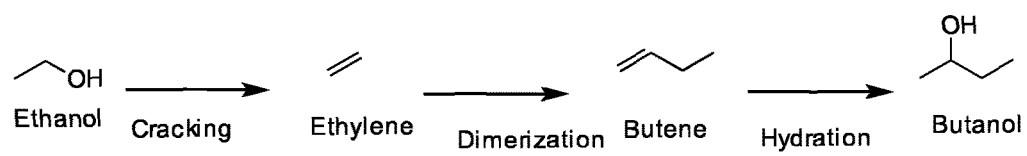
FIG. 6 Synthesis of butanol from ethane.

FIG. 1 Describes the synthesis of higher alcohols from natural gas liquids by dehydrogenation, oxidation and hydrogenation reaction steps. FIG. 2 Describes the synthesis of alcohol from ethane by dehydrogenation, oxidation and hydrogenation. FIG. 3 Describes the synthesis of Higher Alcohols from Natural Gas Liquids. FIG. 4 Describes the synthesis of butanol from ethane. FIG. 5 Describes the synthesis of fuels from natural gas liquids. FIG. 6 Describes the synthesis of butanol from ethanol.

Figure 7:
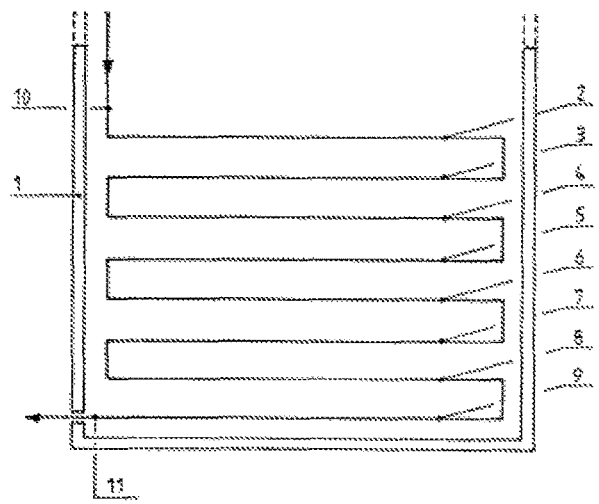
FIG. 7 Steam cracking furnace for natural gas liquids.

FIG. 7 Describes a steam cracking furnace for natural gas liquids incorporated by reference from Steppich et al U.S. Pat. No. 4,237,073 as are FIG. 8 Describes a plant for synthesis of acetaldehyde form ethylene and FIG. 9 Describes a plant with efficient water recycling for synthesis of acetaldehyde form ethylene.

DEFINITIONS

Unless specifically noted otherwise herein, the definitions of the terms used are standard definitions used in the art. Exemplary embodiments, aspects and variations are illustrated in the figures and drawings, and it is intended that the embodiments, aspects and variations, and the figures and drawings disclosed herein are to be considered illustrative and not limiting.

An "alkyl" group is a straight, branched, saturated or unsaturated, aliphatic group having a chain of carbon atoms, optionally with oxygen, nitrogen or sulfur atoms inserted between the carbon atoms in the chain or as indicated. A $(C_1-C_{20})$alkyl, for example, includes alkyl groups that have a chain of between 1 and 20 carbon atoms, and include, for example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, penta-1,4-dienyl, hexa-1,3-dienyl, hexa-1,3,5-trienyl, and the like. An alkyl group may also be represented, for example, as a —$(CR^1R^2)_m$— where $R^1$ and $R^2$ are independently hydrogen or are independently absent, and for example, m is 1 to 8, and such representation is also intended to cover both saturated and unsaturated alkyl groups.

An alkyl as noted with another group such as an aryl group, represented as "arylalkyl" for example, is intended to be a straight, branched, saturated or unsaturated aliphatic divalent group with the number of atoms indicated in the alkyl group (as in $(C_1-C_{20})$alkyl, for example) and/or aryl group (as in $(C_5-C_{14})$aryl, for example) or when no atoms are indicated means a bond between the aryl and the alkyl group. Nonexclusive examples of such group include benzyl, phenethyl and the like.

An "alkylene" group is a straight, branched, saturated or unsaturated aliphatic divalent group with the number of atoms indicated in the alkyl group; for example, a —$(C_1-C_3)$alkylene- or —$(C_1-C_3)$alkylenyl-.

A "cyclyl" such as a monocyclyl or polycyclyl group includes monocyclic, or linearly fused, angularly fused or bridged polycycloalkyl, or combinations thereof. Such cyclyl group is intended to include the heterocyclyl analogs. A cyclyl group may be saturated, partially saturated or aromatic.

An alcohol is a compound with an alkyl or cyclic alkyl group bearing a hydroxyl functional group. Examples of alcohols are methanol, ethanol, propanol, isopropanol, butanol (including 1-butanol, 2-butanol, isobutanol, tert-butanol), pentanol (and its isomers including 1-pentanol, 2-pentanol, 3-pentanol, isopentanol, neopentanol, cyclopentanol, etc) and straight chain, branched and cyclic isomers of other higher alcohols such as hexanol, cyclohexanol, methylcyclohexanol, heptanol (including 1-heptanol, 2-heptanol, 3-heptanol, 4-heptanol, iso-heptanol and other isomers), nonanol, etc. A higher alcohol is an alcohol having two or more carbons.

"Halogen" or "halo" means fluorine, chlorine, bromine or iodine.

A "heterocyclyl" or "heterocycle" is a cycloalkyl wherein one or more of the atoms forming the ring is a heteroatom that is a N, O, or S. Non-exclusive examples of heterocyclyl include piperidyl, 4-morpholyl, 4-piperazinyl, pyrrolidinyl, 1,4-diazaperhydroepinyl, 1,3-dioxanyl, and the like.

"Substituted or unsubstituted" or "optionally substituted" means that a group such as, for example, alkyl, aryl, heterocyclyl, $(C_1-C_8)$cycloalkyl, hetrocyclyl$(C_1-C_8)$alkyl, aryl $(C_1-C_8)$alkyl, heteroaryl, heteroaryl$(C_1-C_8)$alkyl, and the like, unless specifically noted otherwise, maybe unsubstituted or maybe substituted by 1, 2 or 3 substitutents selected from the group such as halo, nitro, trifluoromethyl, trifluoromethoxy, methoxy, carboxy, carboxyester, —$NH_2$, —OH, —SH, —$NHCH_3$, —$N(CH_3)_2$, —SMe, cyano and the like.

The methods of the present invention can comprise, consist of, or consist essentially of the essential elements and limitations of the method described herein, as well as any additional or optional ingredients, components, or limitations described herein or otherwise useful in synthetic organic chemistry.

Synthesis gas or syngas is a mixture of varying amounts of carbon monoxide and hydrogen. Syngas maybe produced by the partial oxidation of materials such as methane, liquid hydrocarbons, coal, biomass, etc.

Biomass is material obtained from living or recently living organisms.

Natural Gas liquids are gaseous hydrocarbons like ethane $(C_2H_6)$, propane $(C_3H_8)$, normal butane (n-$C_4H_{10}$), isobutane (i-$C_4H_{10}$), pentanes and even higher molecular weight hydrocarbons. When processed and purified into finished by-products, all of these are collectively referred to as NGL (Natural Gas Liquids).

In various embodiments, the current invention is directed to novel methods to prepare alcohols, olefins and alkanes. In one embodiment, a lower alkane such as ethane, propane or butane is dehydrogenated to form its olefin derivative. The olefin dimerized in the presence of a catalyst and the resulting product olefin is hydrated over an acidic catalyst to form an alcohol. Said alcohol products can be used individually or as mixtures of compounds as fuels, solvents and chemicals for industry.

In one embodiment, a mixture of ethane, propane and butane are converted to a mixture of ethanol, propanol and butanols. In another embodiment the alkanes are separated into individual components and dehydrogenated, dimerized and hydrated to form alcohols.

In one embodiment, ethanol is dehydrated to form ethylene which is dimerized to form butene and then hydrated over an acidic catalyst to form 2-butanol.

Dehydrogenation may be achieved by thermal or steam cracking or passing hydrocarbons over metal catalysts at elevated temperatures. The steam cracking process and other non-catalytic cracking processes are well known to those of ordinary skill in the art. Steam cracking processes are generally carried out in radiant furnace reactors at elevated temperatures for short residence times while maintaining a low reactant partial pressure, relatively high mass velocity, and effecting a low pressure drop through the reaction zone. Any of the furnaces known to those skilled in the art may be employed, e.g., Palchik et al., U.S. Pat. No. 3,274,978; Hallee et al., U.S. Pat. No. 3,407,789; Woebcke, U.S. Pat. No. 3,820,955; Alagy et al., U.S. Pat. No. 4,780,196; DiNicolantonio, U.S. Pat. No. 4,499,055; Martens, U.S. Pat. No. 4,762,958 and the like. Although radiant furnace reactors are preferred, any high severity steam cracking system known to those of ordinary skill in the art may be employed. The dehydrogenation of ethane may be carried out by cracking to form ethylene.

Various catalysts may be used in the dehydrogenation of lower alkanes. The catalyst may contain a transition metal such as ruthenium, palladium, platinum, rhodium, nickel, iridium, rhenium, copper, zinc, chromium, nickel, iron, cobalt, or combinations of thereof. The catalyst may contain a combination of one or more transition metals and a combination of transition metals with main group elements such as boron, aluminum, gallium or for example copper, chromium and barium; copper, zinc and tin; platinum and tin or ruthenium and tin; etc. The catalyst may contain alkali metal or alkaline earth metal promoters such as potassium, barium, magnesium, etc.

Catalysts used in reductions maybe supported or unsupported. A supported catalyst is one in which the active metal or metals are deposited on a support material e.g. by soaking or wetting the support material with a solution, spraying or physical mixing followed by drying, calcination and finally reduction with hydrogen if necessary to produce the active catalyst. Catalyst support materials used frequently are porous solids with high surface areas such as silica, alumina, titania, magnesia, carbon, zirconia, zeolites, etc.

Various catalysts may be used in hydrogenation reactions. The catalyst may contain a transition metal such as ruthenium, palladium, platinum, rhodium, nickel, iridium, rhenium, copper, zinc, chromium, nickel, iron, cobalt, or combinations of thereof. The catalyst may contain a combination of one or more transition metals and a combination of transition metals with main group elements such as boron, aluminum, gallium or for example copper, chromium and barium; copper, zinc and tin; platinum and tin or ruthenium and tin; etc. The catalyst may contain alkali metal or alkaline earth metal promoters such as potassium, barium, magnesium, etc.

The reduction of olefins by hydrogenation may be done using Raney type sponge catalysts such as Raney nickel, copper, cobalt, etc optionally bearing promoters such as iron, molybdenum, chromium, palladium, etc.

In one embodiment olefins can be hydrated in the presence of a polymer supported acidic catalyst such as Amberlyst or Dowex to form alcohol product.

In one variation, compounds of this invention can be synthesized by the steps outlined in FIG. 1. FIG. 1 describes the synthesis of higher alcohols from natural gas liquids.

In one variation, compounds of this invention can be synthesized by the steps outlined in FIG. 2. FIG. 2 describes the synthesis of butanol from ethane.

In one variation, compounds of this invention can be synthesized by the steps outlined in FIG. 3. FIG. 3 describes formation of synthesis of fuels from natural gas liquids.

In one variation, compounds of this invention can be synthesized by the steps outlined in FIG. 4. FIG. 4 describes synthesis of fuels from ethanol.

In one variation, compounds of this invention can be synthesized by the steps outlined in FIG. 5. FIG. 5 describes synthesis of fuels from ethanol.

In one variation, compounds of this invention can be synthesized by the steps outlined in FIG. 5. FIG. 5 describes synthesis of fuels from ethanol.

EXPERIMENTAL

The following procedures may be employed for the preparation of the compounds of the present invention. The starting materials and reagents used in preparing these compounds are either available from commercial suppliers such as SigmaAldrich, Alfa Aesar, TCI, Linweld gases, etc or are prepared by methods well known to a person of ordinary skill in the art, following procedures described in such references as Fieser and Fieser's Reagents for Organic Synthesis, vols. 1-17, John Wiley and Sons, New York, N.Y., 1991; Rodd's Chemistry of Carbon Compounds, vols. 1-5 and supps., Elsevier Science Publishers, 1989; Organic Reactions, vols. 1-40, John Wiley and Sons, New York, N.Y., 1991; March J.: Advanced Organic Chemistry, 4th ed., John Wiley and Sons, New York, N.Y.; and Larock: Comprehensive Organic Transformations, VCH Publishers, New York, 1989.

Standard organic chemical reactions can be achieved by using a number of different reagents, for example, as described in Larock: Comprehensive Organic Transformations, VCH Publishers, New York, 1989.

Samples were analyzed on a Agilent 6890 5973 GCMS system equipped with a JW1 DB624 column with dimensions of 30 m×250µ×1.4µ column. The method ran at 1 ml/min flow, with oven temperature at 40° C. for the first two minutes followed by temperature ramp at 10° C./min to a temperature of 240° C. which was held for 10 minutes. The solvent delay was set at 5 minutes. Chemical identities of obtained alcohols were confirmed by mass spectroscopic analysis on GCMS against a NIST 2011 library as well as by comparison against commercial standards. Additionally, mixtures were analyzed for lower alcohols by derivatizing the alcohol mixture by dissolving in methylene chloride, adding excess of diisopropylethylamine (DIEA), dimethylamino pyridine (DMAP) and acetyl chloride or acetic anhydride. After standing for 30 minutes the reaction mixture was analyzed by GCMS. An experiment for lower molecular weight alcohol analysis was done as follows. The liquid product (~30 µl) of the reaction was dissolved in 1 ml of methylene chloride, DIEA was added with a 10 µl syringe in increments until the medium was basic, 2 mg of DMAP was added followed by acetyl chloride. The solution was allowed to stand for about a half hour until the alcohols were esterified to their acetyl derivatives. The resulting mixture was analyzed on the GCMS giving a mixture of esters that appeared on GCMS analysis after the solvent delay.

Example 1

A steam cracking furnace (FIG. 5), comprising brickwork thermal radiation (1) formed by a rectangular parallelipiped whose internal dimensions are, length: 9.75 m; width: 1.70 m and height: 4.85 m. Disposed in the enclosure (1) is a nickel and chromium based refractory steel cracking tube having a mean internal diameter of 108 mm, a thickness of 8 mm and, having regard to the capacity of the enclosure (1), a total length of 80 m between the inlet (10) and the outlet (11). The cracking tube is disposed in the form of a coil comprising 8 horizontal straight portions each of equal length which are interconnected via bends. The internal diameter of the sections (2) and (3) situated towards the inlet of the thermal enclosure is 81 mm; the following sections (4) and (5) have an internal diameter of 88 mm and the sections (6) and (7) have an internal diameter of 117 mm; the internal diameter of the sections (8) and (9) situated towards the outlet of the thermal enclosure is 135 mm. The internal diameters of the cracking tube at the inlet (10) and outlet (11) of the enclosure (1) being 81 mm and 135 mm respectively, the ratio between the internal diameters of the tube at the inlet and outlet is therefore 1.7. The reaction volume of the second half of the cracking tube length, corresponding to the straight sections (6), (7), (8), (9), is 1.95 times greater than the reaction volume of the first half of the cracking tube length, corresponding to the straight sections (2), (3), (4) and (5).

The thermal radiation enclosure of the steam cracking furnace is equipped with burners on the walls of the enclosure in five horizontal rows equally spaced out from one another. The total thermal power is distributed between the five rows of burners as follows: 40% of the total thermal power on the first row of burners, disposed at the top of the enclosure adjacent the inlet of the cracking tube, 27% on the second row of burners, disposed immediately below the first row, 18% on the third row of burners, disposed immediately below the second row, 10% on the fourth row of burners, disposed immediately below the third row, and 5% on the fifth row of burners, disposed immediately below the fourth row, adjacent the outlet of the cracking tube. The ratio between the thermal power of the burners applied to the first half of the tube, situated towards the inlet of the enclosure, and that applied to the second half of the tube, situated towards the outlet of such enclosure, is therefore 76/24. A mixture of ethane and steam is passed through the cracking tube. The composition of the mixture of ethane and steam used is such that the ratio by weight between the quantity of ethane and the quantity of steam is 2.25. Ethane is therefore introduced into the cracking tube at a flow rate of 1800 kg/h and steam at a flow rate of 800 kg/h. The cracking temperature of the mixture of ethane and steam rises from 695 to 848° C. at the furnace outlet. Having regard to the distribution of the thermal flux in the enclosure, the thermal power applied to the first half of the cracking tube length, situated towards the inlet of the radiation zone, was 3.1 times greater than that applied to the second half of the tube length, situated towards the outlet of such zone. The mean dwell time of the mixture of ethane and steam flowing in the cracking tube between the inlet and outlet of the radiation zone of the furnace is 530 milliseconds. In these conditions 1200 kg of ethylene is produced per hour and the level of conversion by weight of the steam cracking reaction was 83.5%.

Example 2

A stainless steel autoclave of the Grignard type, of 250 ml capacity with a double jacket, at temperature of 18° C. (adjusted by circulated water) is fed under ethylene atmosphere successively with 2.5 ml of a triethyl aluminum solution in hexenes prepared by admixing 0.25 ml of triethylaluminum with 9.75 ml of hexenes, then with a solution of a tetra-n-butyl titanate-tetrahydrofuran complex prepared by admixing 0.05 ml of tetra-n-butyl titanate with 0.024 ml of tetrahydrofuran and 2.42 ml of hexanes. The molar ratio of the tetrahydrofuran to the titanate was 2.1:1. After 2 minutes of interaction, the temperature is raised to 55° C. and the ethylene pressure to 2 MPa. After 2.5 h ethylene feed is discontinued and the catalyst is destroyed by injecting 2 ml of water under pressure. 133 g of ethylene as a total have been consumed. In addition to the unreacted ethylene, 0.28 g of n-butane, 92.40 g of 1-butene, 6.46 g of hexenes, 0.17 g of octenes and 0.0027 g of polyethylene have been recovered.

Example 3 (from EP 0 561 398)

A stainless steel stirred 300 mL reactor including a 40 mL addition vessel connected to the reactor by an addition valve is agitated at a slow agitation (~300 rpm) during purging or addition of the reagents and at a normal agitation (~1600 rpm) during the reaction. The samples of the reaction mixture (~5 g) are taken from the reactor through its sample valve into a 50 mL pressure sample tube and then analyzed with an 45 HP 5890 II GC-FID Spectrometer equipped with a capillary DB-1 (60 m) column. The column is operated at 30° C. for 5 minutes, followed by a 15° C./minute increase to 285° C. which has been held for 13 minutes. A flame ionization detector in the area percent mode is used.
The reactor is purged with nitrogen for 5 minutes followed by addition of 48 mL of 2,2,2-trifluoroethanol, diphenylphosphine (1.0 mmol) and bis(1,5-cyclooctadiene)nickel(0) (0.275 g; 1.0 mmol). The reactor is sealed, purged with ethylene at least four times, and then pressured with ethylene to 0.45 MPa (50 psig) for 5 minutes. A solution of trifluoroacetic acid (0.1 14 g; 1.0 mmol) in 2 mL of 2,2,2-trifluoroethanol is added to the addition vessel using a syringe. The addition vessel is immediately sealed and pressured to 4.93 MPa (700 psig) with ethylene. The contents of the addition vessel (including ethylene) are transferred to the reactor at the end of the above mentioned 5 minute period through the addition valve. The reaction temperature is ~40° C. by an external cooling water. The internal reactor pressure is about 700 psig and the reaction is continued for ~10 minutes. GC analysis shows 90% wt of the C4 fraction which included 97% wt of the mixture 2-butenes (trans/cis=60/40).

Example 4 Catalyst Preparation 12-tungstosilicic acid (24.370 g) is dissolved in distilled water (800 ml) to which is added orthophosphoric acid (1.488 g of 85% w/w strength). In a separate container $KHCO_3$ (11.15 g) is dissolved in water (50 ml) and then slowly added, with stirring, to the acid solution. The container is rinsed three times with distilled water (50 ml, total volume added 150 ml) and the washings are added to the acid solution. (The quantity of $KHCO_3$ provides one molar equivalent of potassium per mole of 12-tungstosilicic acid $H_2 0$ dissolved in the solution). The solution is stirred for 15 minutes after the evolution of $CO_2$ ceases. Then Grace57 silica (1.21), an essentially pure silica carrier, is added and allowed to soak for 24 hours. After soaking, the catalyst is drained of excess solution for 1 hour and then dried in air for 16 hours at 105° C. One liter of finished catalyst weighs about 551 g, giving an acid loading of 151 g/l. Conditions: One liter of catalyst (acid loading 151 g/l), as prepared above is loaded into the reactor. The plant is started-up, ethylene introduced and conditions were adjusted to target and stabilized. Reactor inlet pressure is 1012 psi and reactor inlet temperature 225° C. with reactor exit temperature 245° C. Ethylene recycle flow rate is 1500 g/hr; reactor inlet water:ethylene mole ratio is 0.387; wash tower water flow rate is 1300 ml/hr running at the ambient temperature of 21 C. The following performance is achieved in the pilot plant by the catalyst: ethanol productivity, 163.5 STY (space-time-yield); diethylether, 7.02 STY; acetaldehyde, 0.60 STY; selectivity to ethanol, 94.6% (selectivity is defined as: the ratio of the moles of ethylene converted to ethanol to the total moles of ethylene converted to products). In a plant utilizing recycled (un-reacted) ethylene the gaseous product exiting the reactor is cooled to 20 C before passing to a high pressure gas-liquid separator for separating the water-rich and ethylene-rich phases. The water-rich phase, which contains a major proportion of the ethanol and also by-products diethylether and acetaldehyde, was passed through a control valve to a collection pot at ambient pressure. The ethylene-rich stream from the gas-liquid separator was then passed to the bottom of the water wash tower where it met a countercurrent stream of water which stripped the majority of the remaining ethanol from the gaseous stream flowing upwards. The purified gaseous stream, which was predominantly ethylene, but contained in the region of 90 mg/l of diethylether, 5 mg/l of acetaldehyde and less than 0.5 mg of ethanol per liter of gas (as measured at normal temperatures and pressures), was then passed to the recycle machine for feeding back to the reactor. The flow of water into the wash tower was in the region of 1300 ml/hr and the level in the tower was maintained by a level control system and liquid off-take control valve. The liquid exiting the wash tower is mixed with the liquid product from the gas-liquid separator and contained the ethanol product of the plant.

Example 5

Figure 8:
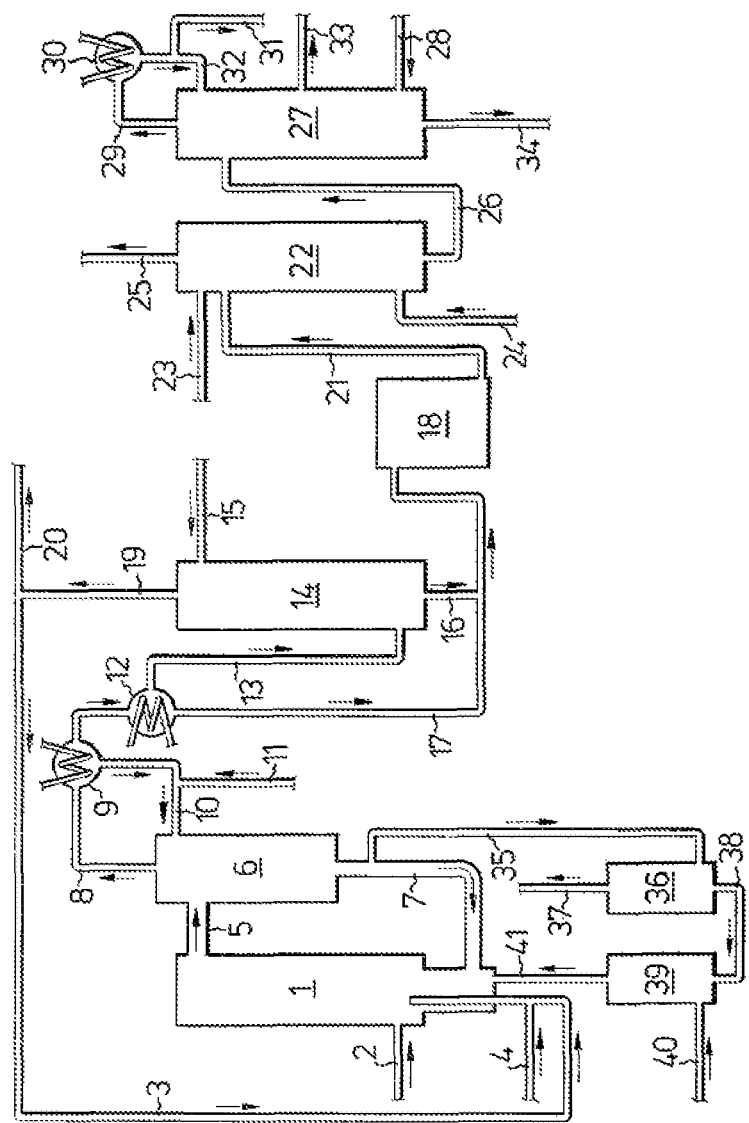
FIG. 8 Describes a plant for synthesis of acetaldehyde form ethylene.
Figure 9:
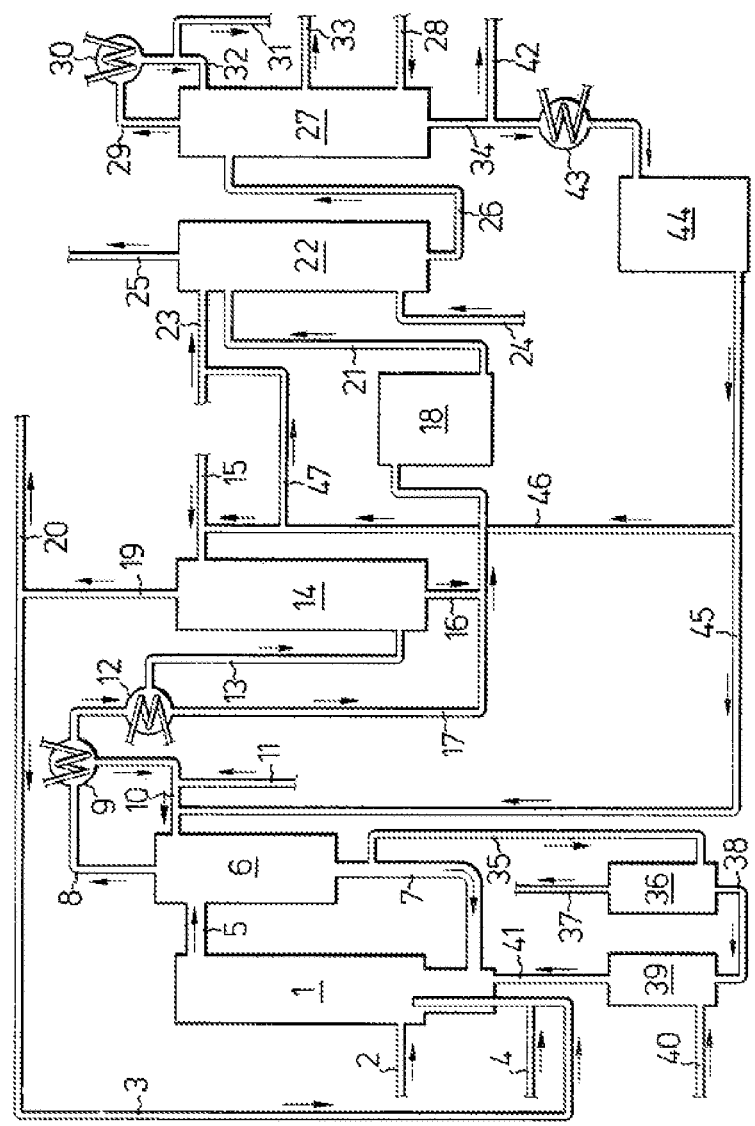
FIG. 9 Describes a plant with efficient water recycling for synthesis of acetaldehyde form ethylene.

Synthesis of Acetaldehyde from Ethylene (FIG. 8). Steppich et al; Process for the manufacture of acetaldehyde U.S. Pat. No. 4,237,073 A. An aqueous solution of $CuCl_2$, $CuCl$ and $PdCl_2$ is placed in reactor (1). Oxygen is added via conduit (2) and circulating gas, to which fresh ethylene is added via conduit (4) is introduced via conduit (3). The gas-liquid mixture formed in the reactor and consisting of gaseous starting and final products and of the catalyst solution passes via tube (5) into separator (6), where the gaseous phase and the liquid phase are separated from each other. The liquid is recycled to reactor (1) via conduit (7). The gases leave the separator via conduit (8) and are cooled to 110° C. in precondenser (9). The condensate formed in this process is recycled to the reactor by passing successively via conduit (10) to the separator, after having added via conduit (11) demineralized water to compensate for the water of the catalyst solution discharged from the reactor in conjunction with the reaction products and via conduit (7). The gases that have not condensed in the precondenser (9) are further cooled in heat exchanger (12) and are then passed to washing tower (14) by passing over conduit (13). Acetaldehyde is washed out from the gases with water introduced via conduit (15). The acetaldehyde solution formed passes via conduit (16) to collecting vessel (18) and the condensate formed in heat exchanger (12) passes via conduit (17) to vessel (18). The washed gases leave the washing tower at the top and are recycled to reactor (1) via conduit (19), after a portion thereof has been discharged as waste gas via conduit (20). The mixture designated as "crude aldehyde" is conveyed to the first distillation column (22) from vessel (18) by passing through conduit (21) and is submitted to an extractive distillation with water. The quantity of water required for this purpose is introduced via conduit (23). The column is heated by steam introduced via conduit (24). The head product mainly consisting of methyl chloride, ethyl chloride, carbon dioxide and ethylene is withdrawn via conduit (25). The bottom product is conveyed to the second distillation column (27) via conduit (26), this column being likewise heated by direct steam which is introduced via conduit (28). Pure acetaldehyde is withdrawn as head product via conduit (29). After having condensed in heat exchanger (30), the main quantity of acetaldehyde is withdrawn via conduit (31) and part thereof is refluxed to column (27) via conduit (32). A fraction substantially consisting of crontonaldehyde is withdrawn at a lateral outlet (33). The high-boiling by-products (in particular acetic acid and chloroacetaldehydes) and the water are withdrawn at the bottom as "waste water" via conduit (34). Part of the liquid recycling to reactor (1) from separator (6) via conduit (7) is withdrawn continuously via conduit (35) and it is released from pressure in the expansion vessel (36). Thereby the dissolved low-boiling substances pass over in the gaseous phase and are removed via conduit (37). The degassed solution is conveyed to regenerator (39) via conduit (38), where it is heated to 170° C. by means of steam introduced via conduit (40). Next, the solution is recycled to reactor (1) via conduit (41). In the plant specified above there are prepared per hour 13 tons of acetaldehyde from 5.3 tons of oxygen and 9 tons of ethylene in the presence of a catalyst solution containing 100 tons of water, 100 kmols of CuCl and $CuCl_2$ and 60 kg $PdCl_2$. The following quantities of water and steam are consumed in this process: 15 m³/h of completely demineralized water for the reactor (to compensate for the losses by evaporation), introduced via conduit (11), 77.5 m³/h of river or spring water to wash out the acetaldehyde, introduced via conduit (15), 1.5 tons/h of direct steam for the catalyst regeneration, introduced via conduit (40), 1.5 m³/h of completely demineralized water for the extraction in the first distillation column, introduced via conduit (23), 3 tons/h of direct steam for the first distillation column, introduced via conduit (24) and 14 tons/h of direct steam for the second distillation column introduced via conduit (28). From these feed quantities of water and steam there results a waste water quantity of 112.5 m³/h, obtained as bottom product of column (27). The waste water is worked up biologically.

Example 6

Apparatus arrangement (cf. FIG. 9) The apparatus arrangement is identical to that in the Comparative Example, except that the waste water withdrawn via conduit (34) at the bottom of the second distillation column (27), after removal of part thereof via conduit (42) is recycled to the process via condenser (43) and storage vessel (44) by the following paths: 1. Via conduit (45) and conduit (10) to separator (6) to compensate for the evaporated water of the catalyst solution, (these losses were off set in the Comparative Example by the addition of completely demineralized water via conduit (11). 2. To washing tower (14) by passing through conduit (46), that branches from conduit (45) and opens into conduit (15) (through this latter conduit fresh water had been introduced in the Comparative Example. In this procedure this addition is required only at the beginning of the process). 3. To the first distillation column (22) by passing through conduit (47) that branches from conduit (46) and opens into conduit (23) (in the Comparative Example fresh water had been introduced via the latter conduit. In this procedure this addition is required at the beginning of the process only). Analogously to the Comparative Example there are prepared per hour 13.0 tons of acetaldehyde with the sole difference that the main quantity of the waste water is recycled.

Example 7

Butene to 2-butanone: Stapp et al; U.S. Pat. No. 4,203,927. The apparatus and general procedure described before Example I are utilized in these runs. In each run the reactor is charged with the indicated amount of 2-butene (a mixture of cis- and trans-isomers), palladium(II) chloride (5 mmoles), a cupric chloride (20 mmoles), hexadecyltrimethylammonium bromide (1.8 mmoles), water (50 ml), and chlorobenzene (50 ml). The amounts of orthoboric acid and 2-butene and the reaction temperatures utilized in these runs, as well as the results obtained in the runs (by glc analysis) are presented in Table V below.

TABLE V

| Run No. | $H_3BO_3$ Mmpls | 2-Butene Mmols | Temp. °C. | 2-Butene Conversion | Methyl ethyl ketone | 3-choloro-2-butanone |
|---|---|---|---|---|---|---|
| | 100 | 202 | 105 | 93 | 75 | 7.2 |
| | 100 | 200 | 90 | 98 | 82 | 2 |
| | 100 | 207 | 75 | 93 | 94 | Trace |
| | 100 | 211 | 60 | 52 | 100 | — |
| | — | 205 | 105 | 66 | 84 | 10 |
| | — | 204 | 75 | 82 | 94 | — |
| | — | 214 | 60 | 71 | 100 | — |

*(a) Amount of methyl ethyl ketone in the reaction product based on the amount of 2butene converted. .sup.(b) Amount of 3chloro-2-butanone in the reaction product based on the amount of 2butene converted. .sup.(c) The reaction mixture also contained 100 mmoles sodium chloride.

The results of Runs 13 through 16 demonstrate operability of the process of this invention for the two-phase oxidation of 2-butene to methyl ethyl ketone at reaction temperatures from about 60° C. to about 105° C. 3-Chloro-2-butanone is a by-product of this reaction at higher reaction temperatures. Control Runs 17, 18, and 19 are without the presence of orthoboric acid.

Example 8

Two runs carried out in which 1-butene is oxidized to methyl ethyl ketone at a reaction temperature of 60° C. The apparatus and general procedure described before Example I are utilized in these runs. In each run, the reactor is charged with the indicated amounts of 1-butene, palladium(II) chloride (5 mmoles), cupric chloride (20 mmoles), hexadecyltrimethyl-ammonium bromide (1.8 mmoles), water (50 ml), and chlorobenzene (50 ml). The amounts of orthoboric acid and 1-butene utilized in these runs and the results obtained in the runs (by glc analysis) are presented in Table below.

| Run No. | $H_3BO_3$ Mmpls | 2-Butene Mmols | 2-Butene Conversion | Methyl ethyl ketone |
|---|---|---|---|---|
|  | 100 | 209 | 57 | 100 |
|  | — | 216 | 65 | 100 |

REFERENCES

1. Cockman et al, Olefin hydration process; U.S. Pat. No. 6,072,090 A
2. Inoue et al, Process for Catalytic Hydration of Olefins U.S. Pat. No. 5,608,123
3. Martens et al, Process and furnace for the steam cracking of hydrocarbons for the preparation of olefins and diolefins; U.S. Pat. No. 4,762,958
4. Jacob Rubin, Flexible light olefins production; U.S. Pat. No. 5,523,502
5. Chauvin et al, Conversion of ethylene into butene-1 using additives based on quaternary ammonium salts; U.S. Pat. No. 5,877,376
6. Ah-Hsiang Wu, Ethylene dimerization; U.S. Pat. No. 5,221,775
7. Stapp et al; U.S. Pat. No. 4,203,927
8. Steppich et al; Process for the manufacture of acetaldehyde U.S. Pat. No. 4,237,073 A.
9. Synthesis of high caloric fuels and chemicals; Henri et al U.S. Ser. No. 13/672,568
10. Catalytic hydrogenation of ketones and aldehydes; Bullock et al WO 2001098238 A2

The entire disclosures of all documents cited throughout this application are incorporated herein by reference.

What is claimed is:

1. A method to synthesize a higher alcohol starting from ethane derived from natural gas liquid compounds comprising the steps of:
   a) Converting the ethane to ethylene by cracking at a temperature between 695 and 898° C.,
   b) Oxidizing the ethylene to form acetaldehyde using a $CuCl_2$, CuCl and $PdCl_2$ catalyst, and;
   c) Hydrogenating the acetaldehyde to form ethanol.

2. The method of claim 1 where the oxidation step is a Wacker oxidation.

3. The method of claim 1 where the hydrogenation catalyst comprises a transition metal selected from ruthenium, copper, zinc, chromium, platinum or a mixture of two or more of them.

4. A method to synthesize a higher alcohol starting from an alkane derived from natural gas liquid compounds comprising the steps of:
   d) Converting the ethane to ethylene by cracking at a temperature between 695 and 898° C.,
   e) Dimerizing said ethylene to form 2-butene with a catalyst comprising diphenylphosphine nickel catalyst at 700 psi and 40 C, and,
   f) Hydrating said 2-butene product with an acid catalyst selected from a heteropoly acid catalyst, a sulfonic acid catalyst loaded on a polymer or resin, a zeolite, an organopolysiloxane with acid functionalization or phosphoric acid doped on alumina to form 2-butanol.

5. The method of claim 4 where the natural gas liquid mixture comprising ethane, propane and is reacted without separation into its individual component gases.

6. The method of claim 4 where said alkane is converted to olefin by thermal cracking.

7. The method of claim 4 where said catalyst employed in dimerization of olefin is comprises a transition metal from nickel or titanium.

8. The method of claim 4 where said catalyst employed in hydration of olefin dimer is an acid catalyst.

9. The method of claim 4 where said higher alcohol is blended with gasoline.

10. The method of claim 4 where said higher alcohol is butanol where:
   a) Converting ethane to ethylene,
   b) Dimerizing ethylene to form butylene, and,
   c) Hydrating butylenes to form butanol.

11. A method of claim 4 where ethane is converted to ethylene by thermal cracking.

12. A method of claim 4 where said catalyst employed in dimerization of ethylene comprises a transition metal selected from nickel or titanium.

* * * * *